(12) United States Patent
Anderson (10) Patent No.: US 9,849,144 B2
(45) Date of Patent: Dec. 26, 2017

(54) GLUTAMINE AND TREHALOSE COMPOSITIONS

(71) Applicant: Healios Oncology Nutrition, LLC, Houston, TX (US)

(72) Inventor: Peter Meade Anderson, Charlotte, NC (US)

(73) Assignee: Healios Oncology Nutrition, LLC, Houston, TX (US)

( * ) Notice: Subject to any disclaimer, the term of this patent is extended or adjusted under 35 U.S.C. 154(b) by 181 days.

(21) Appl. No.: 14/470,545

(22) Filed: Aug. 27, 2014

(65) Prior Publication Data

US 2015/0080331 A1 Mar. 19, 2015

Related U.S. Application Data

(60) Provisional application No. 61/878,084, filed on Sep. 16, 2013.

(51) Int. Cl.
*A61K 31/7016* (2006.01)
*A61K 31/198* (2006.01)

(52) U.S. Cl.
CPC ........ *A61K 31/7016* (2013.01); *A61K 31/198* (2013.01)

(58) Field of Classification Search
CPC .......................... A61K 31/7016; A61K 31/198
USPC ........................................ 514/53; 536/123.13
See application file for complete search history.

(56) References Cited

U.S. PATENT DOCUMENTS

| | | | |
|---|---|---|---|
| 5,438,075 A * | 8/1995 | Skubitz | A61K 31/195 514/563 |
| 5,545,668 A | 8/1996 | Skubitz | |
| 6,479,068 B1 | 11/2002 | Sherratt | |
| 6,734,170 B2 | 5/2004 | Petit, II | |
| 7,041,651 B2 | 5/2006 | Petit, II | |
| 7,547,433 B2 | 6/2009 | Jacob | |
| 7,709,529 B2 | 5/2010 | Klimberg | |
| 7,947,303 B2 | 5/2011 | Kessler | |
| 2004/0176319 A1 * | 9/2004 | Petit, II | A23L 1/3051 514/53 |
| 2004/0265359 A1 | 12/2004 | Sacks | |
| 2005/0059610 A1 | 3/2005 | Wischmeyer | |

FOREIGN PATENT DOCUMENTS

WO    WO/2008/026310 A1 *    3/2008

OTHER PUBLICATIONS

Ilmura et al.; WO 2008026310 A1; Mar. 6, 2008 (Machine-English Translation).*
Lambros et al. (Biochemical and Biophysical Research Communications 405 (2011) 102-106).*
Peterson D.E., Randomized, placebo-controlled trial of Saforis for prevention and treatment of oral mucositis in breast cancer patients receiving anthracycline-based chemotherapy, Cancer 109(2):322-31 (2006).
Déchelotte P., et al., L-alanyl-L-glutamine dipeptide-supplemented total parenteral nutrition reduces infectious complications and glucose intolerance in critically ill patients: the French controlled, randomized, double-blind, multicenter study, Crit Care Med. 34(3):598-604 (2006).
Skubitz K.M., et al., Oral glutamine to prevent chemotherapy stomatitis: A pilot study, J. Lab. Clin. Med. 127(2): 223-8 (1996).
Echigo R., et al Trehalose treatment suppresses inflammation, oxidative stress, and vasospasm induced by experimental subarachnoid hemorrhage, J. Translat. Med. 10:80 (2012).

* cited by examiner

*Primary Examiner* — Shaojia Anna Jiang
*Assistant Examiner* — Michael C Henry
(74) *Attorney, Agent, or Firm* — Boulware & Valoir (57) ABSTRACT

Pharmaceutical compositions comprising glutamine and trehalose for treating side effects to oncology treatments are disclosed.

6 Claims, 3 Drawing Sheets

FIGURE 1

—TREHALOSE—                —GLUTAMINE—

FIGURE 2

—SUCROSE—                  —TREHALOSE—

GLUTAMINE AND TREHALOSE COMPOSITIONS

PRIOR RELATED APPLICATIONS

This application claims priority to 61/878,084, titled "GLUTAMINE & TREHALOSE COMPOSITIONS," filed Sep. 16, 2013 and incorporated by reference in its entirety for all purposes.

FEDERALLY SPONSORED RESEARCH STATEMENT

Not applicable.

REFERENCE TO MICROFICHE APPENDIX

Not applicable.

FIELD OF THE DISCLOSURE

The disclosure generally relates to pharmaceutical compositions for use in conjunction with oncology treatments that help to reduce the incidence of side effects, especially side effects such as mucositis, but the compositions have many additional uses.

BACKGROUND OF THE DISCLOSURE

Mucositis is the painful inflammation and ulceration of the mucous membranes lining the digestive tract, usually occurring as an adverse effect of chemotherapy and radiotherapy treatment for cancer.

As a result of cell death in reaction to chemo- or radiotherapy, the mucosal lining of the mouth becomes thin, may slough off and then become red, inflamed and ulcerated. The ulcers may become covered by a yellowish white fibrin clot called a pseudomembrane. Peripheral erythema is usually present. Ulcers may range from 0.5 cm to greater than 4 cm and the oral ulcers can be severely painful. In grade 3 oral mucositis, the patient is unable to eat solid food, and in grade 4, the patient is unable to consume liquids as well. The ulcers can also become infected, leading to septicemia and death, especially in immuno-compromised patients, which most cancer patients are.

Oral and gastrointestinal (GI) mucositis affects almost all patients undergoing high-dose chemotherapy and hematopoietic stem cell transplantation (HSCT), 80% of patients with malignancies of the head and neck receiving radiotherapy, and a wide range of other patients. About half of all patients develop oral mucositis that becomes so severe that the patient's cancer treatment must be modified, compromising the prognosis. Thus, mucositis is a serious medical complication, preventing full oncology treatment plans from being implemented.

Treatment of mucositis to date has been mainly supportive. Oral hygiene is the mainstay of treatment—patients are encouraged to clean their mouth every four hours and at bedtime, more often if the mucositis becomes worse. Water-soluble jellies can be used to lubricate the mouth. Salt mouthwash can soothe the pain and keep food particles clear so as to avoid infection. Patients are also encouraged to drink plenty of liquids, at least three liters a day, and avoid irritants such as alcohol, citrus, and foods that are hot.

Medicinal mouthwashes may be used such as chlorhexidine gluconate or viscous lidocaine can be used for relief of pain. Palifermin (KEPIVANCE™) is an FDA approved human KGF (keratinocyte growth factor) that has shown to enhance epithelial cell proliferation, differentiation, and migration. Experimental therapies have also been reported, including the use of cytokines and other modifiers of inflammation (e.g., IL-1, IL-11, TGF-beta3), amino acid supplementation (e.g., glutamine), vitamins, colony-stimulating factors, cryotherapy, and laser therapy.

Symptomatic relief of the pain of oral mucositis may be provided by barrier protection agents such as concentrated oral gel products (e.g. GELCLAIR™) CAPHOSOL™ is a mouth rinse that has been shown to prevent and treat oral mucositis caused by radiation and high dose chemotherapy. MUGARD™ is a FDA-approved mucoadhesive oral protectant designed to form a protective hydrogel coating over the oral mucosa while a patient is undergoing chemotherapy and/or radiotherapy cancer treatments to the head and neck. NEUTRASAL™ is an FDA-approved calcium phosphate mouth rinse that has been shown in an open-label, observational registry trial to prevent and reduce the severity of oral mucositis caused by radiation and high dose chemotherapy. The Mayo Clinic has been testing the antidepressant doxepin in a mouthwash to help treat symptoms, as well.

In 2011, the FDA approved EPISIL™ oral liquid for the management and relief of pain of oral lesions with various etiologies. EPISIL™ creates a lipid membrane that mechanically bonds to the oral cavity mucosa to coat and soothe inflammation and ulcerations, and blanket painful lesions.

In a 2012 randomized controlled pilot study involving pediatric patients, topical application of honey was found to reduce recovery time compared to benzocaine gel in grade 2 and 3 chemotherapy-induced oral mucositis to a degree that was statistically significant. In grade 3 oral mucositis, honey was as effective as a mixture of honey, olive oil and propolis, while both treatments were found to reduce recovery time compared to the benzocaine control.

Although there are promising palliative treatments, no drug has a mechanism of action designed to prevent the death of mucosal cells in the first place, and thus all treatments are symptomatic and not truly preventative.

Glutamine (abbreviated as GLN or Q) is one of the standard 20 amino acids. In human blood, glutamine is the most abundant free amino acid, with a concentration of about 500-900 µmol/l. It is not recognized as an essential amino acid, but may become conditionally essential in certain situations, including intensive athletic training, certain gastrointestinal disorders and in various disease states.

In catabolic states of injury and illness, glutamine becomes conditionally essential (requiring intake from food or supplements). Glutamine has been studied extensively over the past 10-15 years, and has been shown to be useful in treatment of injuries, trauma, burns, and treatment-related side effects of cancer, as well as in wound healing for postoperative patients. Glutamine is also marketed as a supplement used for muscle growth in weightlifting, bodybuilding, endurance, and other sports.

Glutamine is also known to have various effects in reducing healing time after operations. Clinical trials have revealed patients on supplementation regimens containing glutamine have improved nitrogen balances, generation of cysteinyl-leukotrienes from polymorphonuclear neutrophil granulocytes, and improved lymphocyte recovery and intestinal permeability (in postoperative patients), in comparison to those that had no glutamine within their dietary regimen, all without any side effects.

Glutamine-enriched diets have also been linked with maintenance of gut barrier function and cell differentiation, suggesting glutamine may help to protect the lining of the gastrointestinal tract or mucosa. People who have inflammatory bowel disease (ulcerative colitis and Crohn's disease) may not have enough glutamine, but the clinical trials to date have not been conclusive.

GLN has been shown to be effective in preventing mucositis, but the literature has provided inconsistent reports as to its efficacy. Since the initial reports, it has been discovered that sugars administered together with glutamine improves cellular uptake by about three orders of magnitude. U.S. Pat. No. 7,041,651 for example shows that 30-50% monosaccharide or disaccharide or combinations thereof increases GLN uptake by 1000 fold when measured in CaCo-2 cells (a caucasian colon adenocarcinoma cell line) in vitro. Thus, early formulations may have failed for lack of uptake and/or degradation, since many were formulated without sugars, e.g., in saline, and since glutamine is subject to enzymatic and chemical hydrolysis. Unfortunately, only a single complex mixture containing 30% sucrose plus a number of other ingredients was tested in U.S. Pat. No. 7,041,651. Therefore, the scope and concentration of carbohydrates that actually exhibit carrier/uptake function remains unknown.

One glutamine formulation was approved as an orphan drug in 2004. NUTRESTORE™ is a powdered glutamine approved for an oral dosage in 8 ounces of water of 5 grams six times daily in combination with recombinant human growth hormone for the treatment of short bowel syndrome. No pharmacokinetic data were provided and a therapeutic concentration has not been established. The package insert does state, however, that single doses of 20-22 g/kg, 8-11 g/kg and 19 g/kg were lethal in mice, rats and rabbits respectively. It is possible and even likely that large doses are provided to compensate both for a short half life and limited uptake, and such large doses were accompanied by common side effects such as urge to empty bowels, gas, abdominal pain, vomiting, and hemorrhoids.

Another early attempt to formulate a useful pharmaceutical is described in U.S. Pat. No. 5,438,075 and known as "SAFORIS™." This drug was formulated as a suspension containing 500 mg/ml glutamine, 30% sucrose, 2.5% glycerin, 2.8% sorbitol, 0.04% citric acid, 0.36% NaPO$_4$, 0.16% cellulose and carboxymethylcellulose, 0.04% carrageenan, and 0.04% xanthum gum. An NDA for SAFORIS™ was submitted in 2006, but was not granted due to concerns about adverse cariogenic effects of sucrose, as well as diabetic side effects of frequent ingestions of sucrose.

Thus, what is needed in the art are better treatment regimes and better formulations for delivery of glutamine for the prevention and/or treatment of mucositis and other epidermal or gastrointestinal disorders, and for the general nutritional support of cells under stress.

SUMMARY OF THE DISCLOSURE

The invention relates to a formulation of GLN for the treatment of mucositis that contains GLN and trehalose as the two main active ingredients.

Glutamine is a known active agent, needed for cellular support in times of stress.

Trehalose is a natural alpha-linked disaccharide formed by an α,α-1,1-glucoside bond between two α-glucose units. The non-reducing disaccharide trehalose (aka α-D-glucopyranosyl-1,1-α-D-glucopyranoside) is one of the most important storage carbohydrates, which is present in almost all forms of life except mammals.

Trehalose has significant advantages over other disaccharides for the uptake of GLN, namely that it has a good taste, provides reduced concerns regarding dental caries, and has a longer half life in acid, and, perhaps most important, does not have the same effects on insulin levels that an equivalent dose of sucrose does. Trehalose has the added advantage of being an antioxidant and it may also have anti-inflammatory properties (Echigo 2012; Taya 2009). Thus, in addition to somehow assisting in GLN uptake, trehalose itself may have therapeutic effects.

Another important advantage of trehalose, is that it is not broken down in the saliva. Trehalase is the glycoside hydrolase enzyme that catalyzes the conversion of trehalose to glucose. Mammals do have trehalase, but it is located in the kidney and in the intestinal mucosa, and not in the saliva. This is unlike sucrase, which is found in the saliva in mammals, as well as in the intestine. Sucrase can thus begin to catabolize the breakdown of sucrose as soon as it contacts saliva. Further, it is now known that the monosaccharides have no effect on GLN uptake, the sucrase present in saliva can greatly diminish the amount of drug available, both orally and throughout the gastrointestinal tract. Trehalase, being absent from the saliva, allows more of the intact disaccharide to serve its important uptake function as it descends the gastrointestinal tract.

All of these features ensure that a GLN composition where sucrose is partially or completely replaced with trehalose will be absorbed sufficiently, without raising the same concerns that other sugars raise, providing a stable formulation that can survive the acidic environment in the stomach, thus reaching the lower portions of the gastrointestinal tract in active form and possibly also directly contributing to efficacy by suppressing inflammation.

Also provided herein are methods of treating epidermal or gastrointestinal lesions, by administering the compositions of the invention. A particularly important use is in the treatment of mucositis, but the formulations can be administered wherever the cells are in stress and glutamine has become conditionally essential.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, buffers, flavoring agents, flowing agents, and the like.

The following abbreviations are used herein:

| ABBREVIATION | TERM |
| --- | --- |
| GLN or Q | L-glutamine |

DETAILED DESCRIPTION

The disclosure provides novel compositions combining glutamine and trehalose together with pharmaceutically acceptable carriers.

Trehalose is available in bulk from Cargill, which has licensed an enzymatic process for high-yield, large-scale production of trehalose directly from starch at a fraction of the cost of prior methods. Thus, trehalose use is much more cost effective than it was in the past.

Figure 1:
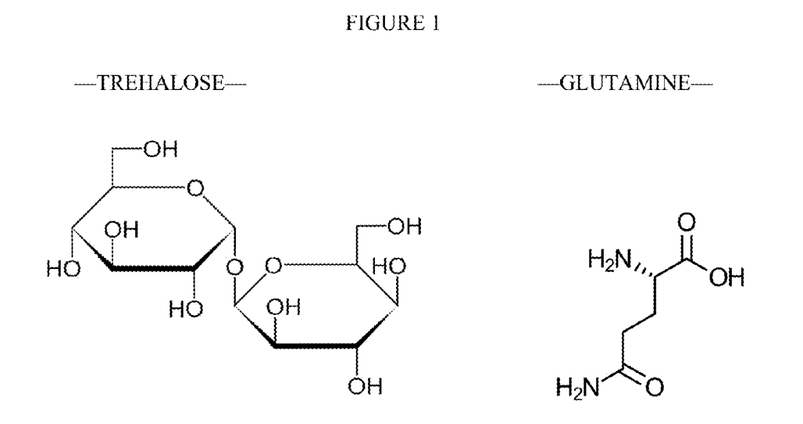
FIG. 1 provides the structures of trehalose (left) and glutamine (right).
Figure 2:
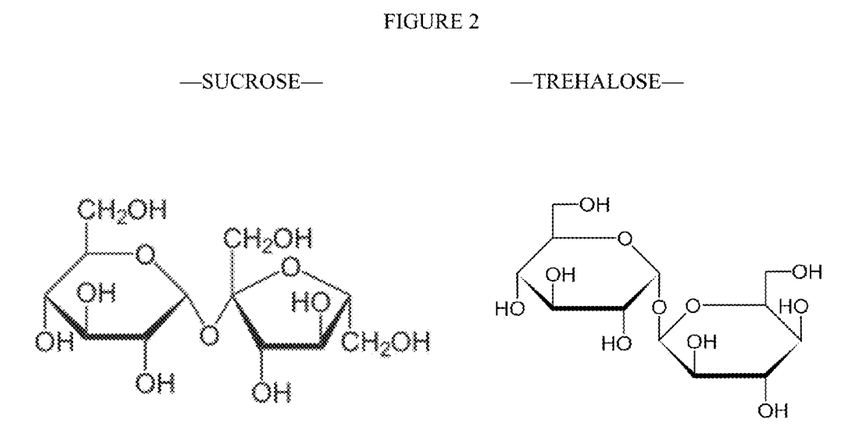
FIG. 2 provides the structure of sucrose (left) in comparison with trehalose (right).
Figure 3:
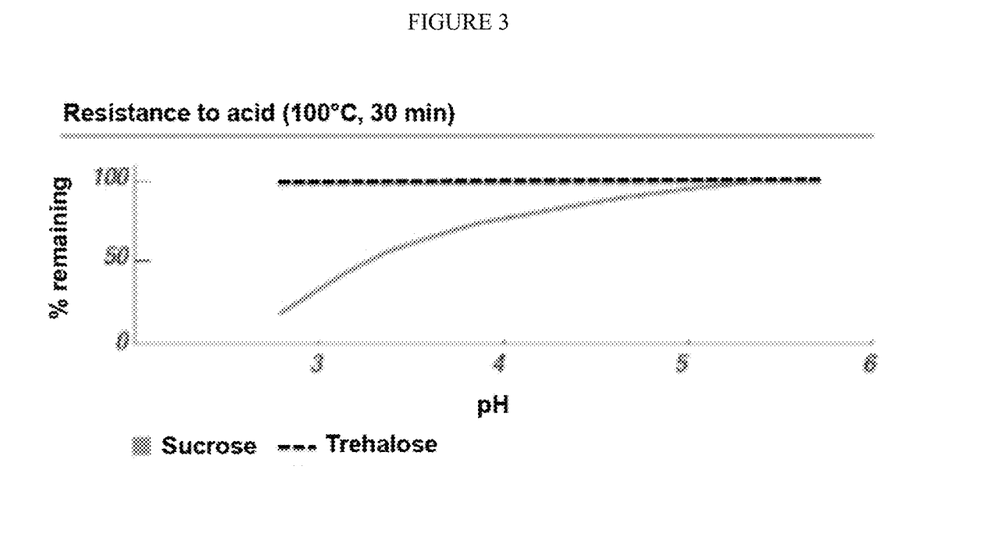
FIG. 3 displays the resistance of trehalose and sucrose to acid.
Figure 4:
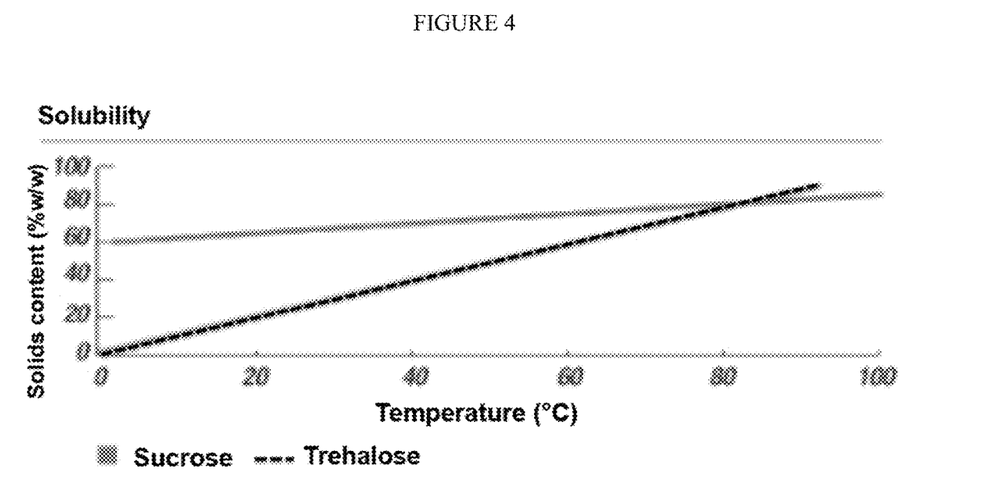
FIG. 4 shows the solubility trehalose and sucrose with temperature.

According to Cargill, trehalose has a number of useful qualities that make its use in foods and pharmaceuticals desirable. Trehalose has been shown to provide superior stabilization of proteins and biological systems, protecting against damage caused by desiccation or freezing. Plus, trehalose remains stable under low pH conditions, even at elevated temperatures (see FIG. 3). Unlike other disaccharides, such as sucrose, trehalose will not readily hydrolyze to its component parts and subsequently it will not take part in Maillard reactions with amino acids and proteins, and it will remain intact throughout much of the gastrointesinal tract, able to serve its GLN uptake function. The high stability of trehalose also enables the original product characteristics (flavor and color) to be retained even after heat processing and prolonged storage.

Trehalose is only 45 percent as sweet as sucrose, delivering balanced taste without masking other flavors in the formulation. It has a clean taste profile with no aftertaste and a sweetness profile that is characterized by a rapid onset of sweetness with comparable persistence to sucrose. Yet, it has lower cariogenic potential (Neta 2000), and thus obviates some of the concerns expressed by reviewers for prior formulations.

Trehalose is readily soluble in water. It is characterized by lower solubility at low temperatures but higher solubility than sucrose at high temperatures. Crystalline trehalose is stable and remains free flowing up to 94% relative humidity. Thus, it can reduce product caking. Products coated with trehalose have enhanced stability, benefiting from the low hygroscopicity of the coating.

Trehalose also has a high glass transition temperature compared with other disaccharides. This property, combined with its high process stability and low hygroscopicity, makes trehalose ideal as a protein protectant and ideally suited as a carrier for spray-dried flavors.

Trehalose will depress the freezing point of a product to the same extent as sucrose. It can therefore be used in frozen foods including ice cream to modify texture whilst providing only mild sweetness.

Figure 5:
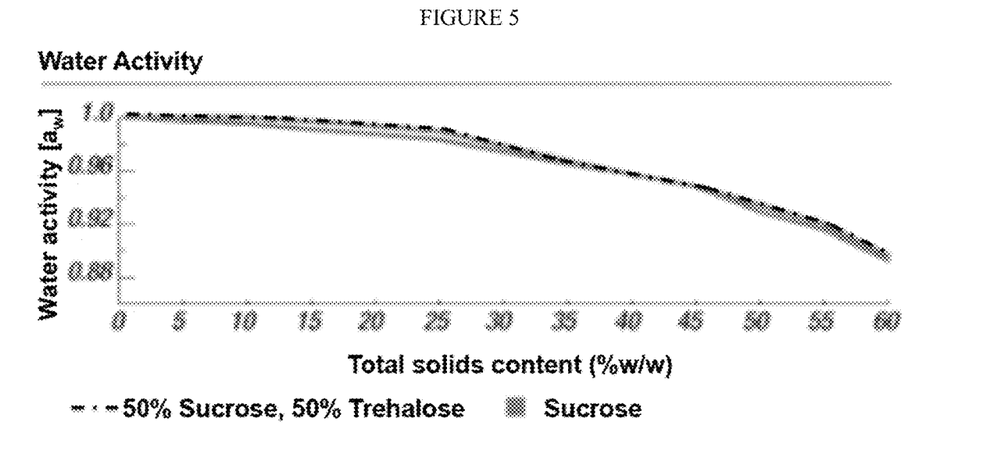
FIG. 5 shows the water activity of trehalose and sucrose with temperature.

Trehalose reduces water activity to the same extent as sucrose. It can therefore be used in combination with sucrose to optimize sweetness while maintaining product shelf life. See e.g., FIG. 5.

Figure 6:
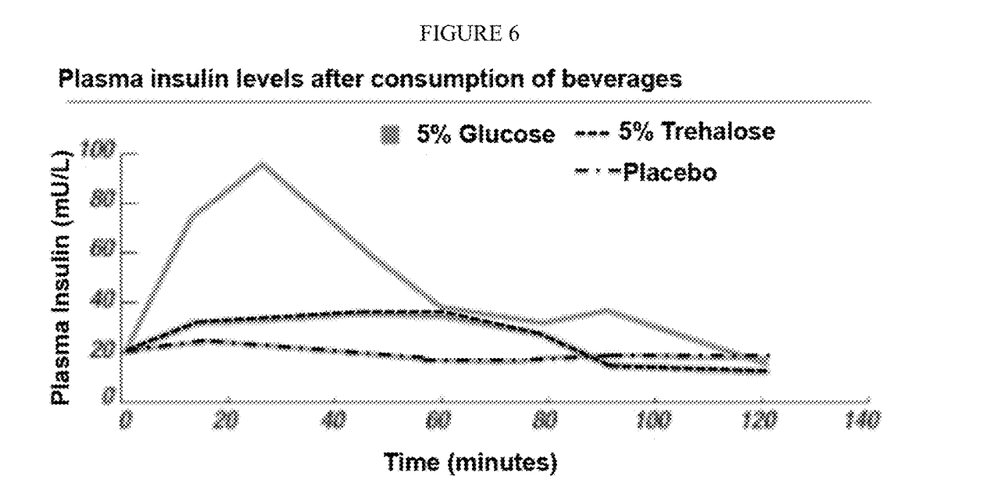
FIG. 6 shows the effect of trehalose and sucrose on plasma insulin levels after consumption of an equivalent dose.

In addition to superior stability, trehalose provides reduced glycemic and insulinemic responses following trehalose injection (van Can 2012, see also FIG. 6). Thus, a trehalose formulation can be safely used several times daily as needed to prevent and or treat mucositis, without raising concerns about diabetes. Thus, the formulation will be much safer to a population with increasing susceptibility to diabetes.

The following exemplary formulations can be prepared by mixing dry powders and milling as necessary:

TABLE 1

Exemplary formulations

| INGREDIENT | g/SERVING (% DRY WT) | g/SERVING (% DRY WT) | g/SERVING (% DRY WT) | g/SERVING (% DRY WT) | g/SERVING (% DRY WT) |
|---|---|---|---|---|---|
| Flavorings and excipients | 10 | 10 | 10 | 10 | 10 |
| L-Glutamine | 10 (20%) | 10 (20%) | 10 (20%) | 20 (40%) | 15% (30%) |
| Sucrose | 0 | 10 (20%) | 15 (30%) | 0 | 0 |
| Trehalose | 30 (60%) | 20 (40%) | 15 (30%) | 20 (40%) | 25 (50%) |
| TOTAL | 50 | 50 | 50 | 50 | 50 |

TABLE 2

Exemplary formulations

| INGREDIENT | g/SERVING (% DRY WT) | g/SERVING (% DRY WT) | g/SERVING (% DRY WT) | g/SERVING (% DRY WT) | g/SERVING (% DRY WT) |
|---|---|---|---|---|---|
| Flavorings and excipients | 10 | 10 | 10 | 10 | 10 |

TABLE 2-continued

Exemplary formulations

| INGREDIENT | g/SERVING (% DRY WT) | g/SERVING (% DRY WT) | g/SERVING (% DRY WT) | g/SERVING (% DRY WT) | g/SERVING (% DRY WT) |
|---|---|---|---|---|---|
| L-Glutamine | 10 (20%) | 10 (20%) | 10 (20%) | 10 (20%) | 10 (20%) |
| Other sugars or sweeteners | 10 palatinose (20%) | 15 palatinose (30%) | 10 honey (20%) | 15 honey (30%) | 2 stevia |
| Trehalose | 20 (40%) | 15 (30%) | 20 (40%) | 15 3(30%) | 28 (56%) |
| TOTAL | 50 | 50 | 50 | 50 | 50 |

TABLE 3

Exemplary formulations

| INGREDIENT | g/SERVING (% DRY WT) | g/SERVING (% DRY WT) | g/SERVING (% DRY WT) |
|---|---|---|---|
| L-Arginine (Base) | 0.12 | .12 | .12 |
| Citric Acid Anhydrous | 0.1 | .1 | .1 |
| DL-Malic Acid | 0.5 | .5 | .5 |
| L-Glutamine | 8 (35%) | 8 (35%) | 8 (35%) |
| Flavorant | 1 | 1 | 1 |
| Stevia (95% Steviosides) | 0.1 | .1 | .1 |
| Beta Carotene (16,700 IU/g) | 0.05 | .05 | .05 |
| Silica | 0.005 | .005 | .005 |
| Sucrose | 10 (44%) | 2.57 (11%) | 0 |
| Trehalose | 2.57 (11%) | 10 (44%) | 12.57 (55%) |
| Carbopol ™ (Polymer) | 0.25 | .25 | .25 |
| TOTAL | 22.8 | 22.8 | 22.8 |

For use, the dry powders are reconstituted as suspensions in e.g., 50-100 ml of water or warm water, swished in the mouth for 10 seconds, and swallowed. Less water, e.g., 10-20 ml can be used if increased sweetness or smaller volume is desired. Additionally, where lesions are pharyngeal, a more concentrated solution should be used than for oral lesions.

The formulation can be used daily, twice daily, four times a day or even 6 times a day, depending on the disease state. For mucositis, frequent smaller doses are more beneficial than one large bolus.

Dosage rates will vary based on the disease state and other confounding factors. However, suitable dosage rate to date is about 1 g/kg/day, and studies demonstrate that up to 40 grams a day have no safety or toxicity concerns. Others recommend lower amounts such as 0.1-0.3 or 0.5 g glutamine per kg body weight per day.

The formulation was specifically contemplated for use in treating mucositis and other epidermal lesions, such as shingles or burns, where glutamine, which is a major energy source for mucosal epithelial cells and stimulates mucosal growth and repair, can both prevent and help heal lesions. It also has application in a variety in digestive system conditions, such as stomach ulcers, ulcerative colitis, and Crohn's disease.

However, intravenous glutamine supplementation is standard care when parenteral nutrition is given for critical illness (Wernerman 2011), and published results indicate the value of glutamine support in a number of diseases, including nerve pain (neuropathy), muscle and joint pains, in protecting the immune system and digestive system in a variety of chemical, radiation and immunosuppressant therapies, for improving recovery after transplant, surgery or traumatic injuries, and preventing infections in critically ill people. GLN has also been used to treat depression, moodiness, irritability, anxiety, insomnia, muscle wasting, attention deficit-hyperactivity disorder (ADHD), a urinary condition called cystinuria, sickle cell anemia, and for alcohol withdrawal support.

Thus, the formulations provided herein can be used anywhere where GLN supplementation can provide therapeutic benefit or nutritional support for stressed cells.

The preferred active ingredient is L-glutamine, but racemic mixtures may be used, as well as pharmaceutically acceptable salts and analogs thereof. However, L-glutamine is generally recognized as safe (GRAS) and is readily available. Indeed 21 CFR 172.320 allows L-glutamine in the free, hydrated or anhydrous form or as the hydrochloride, sodium or potassium salts to be added to food.

In another embodiment, dipeptides such as L-alanyl-L-glutamine (GRAS) or L-glycyl-L-glutamine may be used, since evidence suggests they are water soluble, stable and readily uptaken by dipeptide transport carriers. Other dipeptides include the GRAS substance L-theanine aka N-ethyl-L-glutamine or L-glutamic acid-monoethylamide, and more can be made and tested for efficacy.

Further, although we have formulated a dry powder to be suspended or solubilized and administered orally, the combination of GLN and trehalose can be administered in any suitable way, including topically, enterally, enterically parenterally, by injection, intradermal, intramuscular, intravenous, subcutaneous, nasal, intraperitoneal, intravaginal, intravesically, sublingually, and the like. Further, other dosage forms can be used, including capsules, tablets, drops, gastric feeding tube, duodenal feeding tube, gastrostomy, suppository, enema, and the like. The most suitable choice of routes will depend on the disease, the condition of the patient and on what other active ingredients may be co-administered along with the GLN and trehalose.

In a powder formulation for use as described herein, the GLN can be 1-50% of the dry weight, but is preferably about 5-40% or 10-35%. The disaccharide to GLN ratio should be about 1:1 to 10:1, preferably 2:1 to 5:1 for adequate uptake. The disaccharide can be 10-100% trehalose, although sucrose and other sugars can also be included for their taste qualities.

When formulated or reconstituted as a fluid for oral use, the formulation can be made to have a viscosity greater than water, thus allowing the formulation to more effectively coat the mucosal tissues. A variety of polymers are available to bring the viscosity to e.g., viscosity of at least 100 cP, or preferably 1000 cP or 5,000 cP at 37° C. ASTM D 445 is used to measure viscosity.

U.S. Pat. No. 7,547,433 in particular describes a pseudoplastic liquid composition for treating or inhibiting an oral mucocutaneous disorder, said liquid composition remaining liquid when shear is applied due to swishing the liquid in the mouth; but attaches to and coating the oral mucosa upon discontinuance of said shear. This patent describes the use of wherein the mucoadhesives that include one or more linear or cross-linked polymer(s) selected from the group consisting of polyacrylic acid, carbopol, carboxymethylcellulose, hydroxyalkylcellulose, dextran sulfate, chitosan, and a water-soluble vinyl polymer.

Another formulation that can be beneficial for the treatment of mucositis is a lozenge. Solid lozenges are well known in the drug delivery field. In addition to the matrix and drug, a lozenge may contain other ingredients known in such dosage forms such as acidity regulators, opacifiers, stabilizing agents, buffering agents, flavorings, sweeteners, coloring agents and preservatives. For example, solid formulations may be prepared as lozenges by heating the lozenge base (e.g., a mixture of honey and trehalose) under vacuum to remove excess water and the remaining components are then blended into the mixture. If necessary, the trehelose can be blended in after the honey is heated sufficiently to solidify when heat is removed. The resulting mixture is then drawn into a continuous cylindrical mass from which the individual lozenges are formed. The lozenges are then cooled, subjected to a visual check and packed into suitable packaging.

Another oral delivery system suitable for use in accordance with the present invention is a dissolvable strip. An example of such a device is the Cool Mint Listerine PocketPaks® Strips, a micro-thin starch-based film impregnated with ingredients found in Listerine® Antiseptic (Thymol, Eucalyptol, Methyl Salicylate, Menthol). Non-active strip ingredients include pullulan, flavors, aspartame, potassium acesulfame, copper gluconate, polysorbate 80, carrageenan, glyceryl oleate, locust bean gum, propylene glycol and xanthan gum.

Pharmaceutically active compounds which may be combined with the formulations of the current invention, either for topical treatment of a mucosa, or for transfer of the pharmaceutically active ingredient to the systemic circulation can include, either alone or in combination, one or more of the following classes of drugs: anti-allergy compounds, anti-inflammatory analgesic agents, steroidal and non-steroidal anti-inflammatory agents, anabolic steroids, analgesics, antihistamines, local anesthetics, bactericides and disinfectants, vasoconstrictors, hemostatics, chemotherapeutic agents, antibiotics, antifungal agents, keratolytics, cauterizing agents, antiviral drugs, vitamins, cytokines, and the like. Other classes of pharmaceutically active agents may also be formulated with the formulations described herein.

Examples of anti-inflammatory analgesic agents include acetaminophen, methyl salicylate, monoglycol salicylate, aspirin, mefenamic acid, flufenamic acid, indomethacin, diclofenac, alclofenac, diclofenac sodium, ibuprofen, ketoprofen, naproxen, pranoprofen, fenoprofen, sulindac, fenclofenac, clidanac, flurbiprofen, fentiazac, bufexarnac, piroxicam, phenylbutazone, oxyphenbutazone, clofezone, pentazocine, mepirizole, tiaramide hydrochloride, etc.

Examples of steroidal anti-inflammatory agents include hydrocortisone, predonisolone, dexamethasone, triamcinolone acetonide, fluocinolone acetonide, hydrocortisone acetate, predonisolone acetate, methylpredonisolone, dexamethasone acetate, betamethasone, betamethasone valerate, flumetasone, fluorometholone, beclomethasone diprorionate, etc.

Examples of anabolic steroids include testosterone and oxandrolone.

Examples of antihistamines include diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, etc.

Examples of local anesthetics include dibucaine hydrochloride, dibucaine, lidocaine hydrochloride, lidocaine, benzocaine, p-buthylaminobenzoic acid 2-(di-ethylamino)ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine, dyclonine hydrochloride, etc.

Examples of bactericides and disinfectants include thimerosal, phenol, thymol, benzalkonium chloride, benzethonium chloride, chlorhexidine, povidone iodide, cetylpyridinium chloride, eugenol, trimethylammonium bromide, etc.

Examples of vasoconstrictors include naphazoline nitrate, tetrahydrazoline hydrochloride, oxymetazoline hydrochloride, phenylephrine hydrochloride, tramazoline hydrochloride, etc.

Examples of hemostatics include thrombin, phytonadione, protamine sulfate, aminocaproic acid, tranexamic acid, carbazochrome, carbaxochrome sodium sulfanate, rutin, hesperidin, etc.

Examples of chemotherapeutic drugs include sulfamine, sulfathiazole, sulfadiazine, homosulfamine, sulfisoxazole, sulfisomidine, sulfamethizole, nitrofurazone, taxanes, platinum compounds, topoisomerase I inhibitors, and anthracycline.

Examples of antibiotics include penicillin, meticillin, oxacillin, cefalotin, cefalordin, erythromeycin, lincomycin, tetracycline, chlortetracycline, oxytetracycline, metacycline, chloramphenicol, kanamycin, streptomycin, gentamicin, bacitracin, cycloserine, and clindamycin.

Examples of antifungal agents include polyene antifungals, such as amphotericin b, candicidin, filipin, hamycin, natamycin, nystatin and rimocidin. Imidazole antifungals include bifonazole, butoconazole, clotrimazole, econazole, fenticonazole, isoconazole, ketoconazole, miconazole, omoconazole, oxiconazole, sertaconazole and sulconazole. Triazole and thiazole antifungals include albaconazole, fluconazole, isavuconazole, itraconazole, posaconazole, ravuconazole, terconazole, voriconazole and abafungin. Allylamines and echinocandins include amorolfin, butenafine, naftifine, terbinafine and anidulafungin, caspofungin or micafungin.

Examples of antiviral drugs include protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

Examples of anti-allergy compounds include alopatadine, astemizole, cromolyn, fenpiprane, repirinast, tranilast, traxanox, etc.

Active ingredients that are already in use to treat mucositis can be advantageously mixed with the compositions described herein. Such active ingredients include honey, which is sweet and viscous, and has been published for use in treatment of mucositis. Another potentially active ingredient is sodium. Sodium can relieve pain, and may also have functional effect on uptake using certain GLN transporters. Chlorhexidine gluconate and lidocaine can also be added for disinfection and pain. Cytokines and other modifiers of inflammation (e.g., IL-1, IL-11, TGF-beta3), human KGF, vitamins, colony-stimulating factors, may also prove beneficial, as can various barrier agents and/or thickeners.

GLN Uptake

The effectiveness of amino acid supplementation has been limited in some individuals due to aging or disease. Effective supplementation with certain amino acids is further limited to varying degrees by the low aqueous solubility and limited cellular uptake of some amino acids. Glutamine, for example, exhibits a low solubility in water (48 g/l at 30° C., 26 g/l at 18° C., 18 g/l at 0° C.) and a low chemical stability in aqueous solution (11 days at 22-24° C.). It also has limited stability in the acidic environment of the gut.

While its has been shown that glucose containing disaccharides, such as sucrose and trehalose, increase GLN uptake by a thousand fold, the mechanism of such increased uptake is not yet clear. Further, the optimal disaccharide/GLN ratio has not yet been determined.

Glutamine uptake in cell lines can be assessed by incubating glutamine plus trehalose with various cell lines, such as HELA cells, HEPG2 cells, and especially cell lines derived from the gastrointestinal tract, such as TC-7, LS 174T, CaCo-2 cells, and the like. GLN can be radiolabelled, uptake allowed to proceed for 15 minutes, cells collected washed twice and radioactivity associated therewith counted. In this way, the optimal ratio of GLN to trehalose can be determined and used in formulating a composition for use in clinical trials.

Clinical Trials

Patients at risk of mucositis can be administered a suspension of L-glutamine as shown in the formulation tables above by mixing with 50-100 ml water, swish and swallow twice a day, from day 1 of chemotherapy for 28 days or for 4 days past the resolution of any post-chemotherapy mucositis. The suspension may be stored in a refrigerator during use for a maximum of 1 month.

The study can be performed as a double-blind, placebo-controlled trial in which L-aspartate, or L-glycine, adjusted to the same pH, mixed in the same vehicle as the glutamine, can be used as the placebo. A proper placebo should be isocaloric, as well as isonitrogenous and of the same liquid volume.

Five parameters will be documented at the end of each course of chemotherapy: 1) total number of days of mucositis, 2) severity of mucositis (numbers of days at each grade), 3) whether the use of glutamine allowed the administration of a dose of chemotherapy that would otherwise not have been tolerable without glutamine, 4) the patient's subjective impression as to whether the mucositis was less severe with glutamine supplementation, and 5) the nadir neutrophil count.

The severity of mucositis is graded as: 0, no mucositis; 1, painful mucositis not necessitating a change in oral intake; 2A, painful mucositis restricting intake to soft foods; 2B, painful mucositis restricting oral intake to liquids; and 3, mucositis preventing oral intake (CALGB criteria). Maximum grade of mucositis and total number of days of mucositis are compared by the paired t-test.

In addition, pharmacokinetic data should be gathered to determine GLN concentration in blood and urine over time. Such data can be gathered in healthy individuals, and also in those individuals undergoing chemo- or radiation-therapy.

The following are incorporated herein by reference in their entirety for all purposes:

Neta T., et al., Low-cariogenicity of trehalose as a substrate, J. Dent. 28 (8):571-6 (2000).
van Can, J. G. P., et al. Reduced glycaemic and insulinaemic responses following trehalose and isomaltulose ingestion: implications for postprandial substrate use in impaired glucose-tolerant subjects, Br. J. Nutr. 108 (7):1210-7 (2012).
Vidal-Casariego A., et al. Efficacy of glutamine in the prevention of oral mucositis and acute radiation-induced esophagitis: a retrospective study, Nutr Cancer. 65 (3): 424-9 (2013) ("Overall, glutamine was associated with a significant reduction of mucositis").
Peterson D. E., Randomized, placebo-controlled trial of Saforis for prevention and treatment of oral mucositis in breast cancer patients receiving anthracycline-based chemotherapy, Cancer 109 (2):322-31 (2007).
Wernerman J., Glutamine supplementation, Annals of Intensive Care 1:25 (2011).
Déchelotte P., et al., L-alanyl-L-glutamine dipeptide-supplemented total parenteral nutrition reduces infectious complications and glucose intolerance in critically ill patients: the French controlled, randomized, double-blind, multicenter study, Crit. Care Med. 34 (3):598-604 (2006)
Skubitz K. M., et al., Oral glutamine to prevent chemotherapy stomatitis: A pilot study, J. Lab. Clin. Med. 127 (2): 223-8 (1996).
Anderson P. M., et al., Effect of low-dose oral glutamine on painful stomatitis during bone marrow transplantation. *Bone Marrow Transplant* 22 (4): 339-44 (1998).
Echigo R., et al Trehalose treatment suppresses inflammation, oxidative stress, and vasospasm induced by experimental subarachnoid hemorrhage, J. Translat. Med. 10:80 (2012).
Taya K., Trehalose inhibits inflammatory cytokine production by protecting IkappaB-alpha reduction in mouse peritoneal macrophages, Arch Oral Biol. 54 (8):749-56 (2009).
U.S. Pat. No. 5,438,075 U.S. Pat. No. 5,545,668 by Skubitz
U.S. Pat. No. 7,547,433
US20050090451, US20100152130, U.S. Pat. No. 7,709,529
U.S. Pat. No. 7,709,529 by Klimberg
U.S. Pat. No. 6,734,170 U.S. Pat. No. 7,041,651
U.S. Pat. No. 6,479,068
U.S. Pat. No. 7,947,303
US20020973105
US20050059610
US20040265359

The invention claimed is:

1. A method of treating epidermal or gastrointesinal lesions, comprising administering a pharmaceutical composition comprising glutamine at 10-40% dry weight and trehalose at 10-60% dry weight and a pharmaceutically acceptable carrier to a patient having epidermal or gastrointesinal lesions.

2. A method of treating or preventing mucositis, comprising swishing a liquid comprising a pharmaceutical composition comprising glutamine at 10-40% dry weight and trehalose at 10-60% dry weight and a pharmaceutically acceptable carrier reconstituted or formulated as a viscous fluid of at least 100 cP at 37° C. in a patient's mouth, said patient being at risk of having or having mucositis, and swallowing the liquid.

3. A method of treating or preventing mucositis, comprising: i) a patient at risk of or having mucositis swishing a liquid pharmaceutical composition comprising glutamine at 10-40% dry weight and trehalose at 10-60% dry weight and a pharmaceutically acceptable carrier in said patient's mouth, and ii) said patient swallowing said liquid.

4. A method of providing cellular nutritional support, comprising administering a pharmaceutical composition comprising glutamine at 10-40% dry weight and trehalose at 10-60% dry weight and a pharmaceutically acceptable carrier to a patient having cellular stress in an amount sufficient to provide cellular nutritional support.

5. A method of treating oral mucositis, comprising swishing a liquid comprising a pharmaceutical composition comprising glutamine glutamine at 10-40% dry weight and trehalose at 10-60% dry weight and a pharmaceutically acceptable carrier formulated as a viscous fluid of at least 100 cP at 37° C. in a patient's mouth, said patient having mucositis, and said patient swallowing the liquid.

6. A method of treating oral mucositis, said method comprising:
  i) swishing a liquid pharmaceutical composition comprising glutamine at 10-40% dry weight and trehalose at 10-60% dry weight and a pharmaceutically acceptable carrier in a mouth of a patient having mucositis, and ii) swallowing said liquid.

* * * * *